(12) United States Patent
Bisti et al.

(10) Patent No.: US 10,092,585 B2
(45) Date of Patent: Oct. 9, 2018

(54) COMPOSITIONS BASED ON SAFFRON FOR THE PREVENTION AND/OR TREATMENT OF CORNEAL DYSTROPHIES

(71) Applicant: Hortus Novus SRL, L'Aquila (IT)

(72) Inventors: Silvia Bisti, Genoa (IT); Evelyne Sernagor, Newcastle upon Tyne (GB)

(73) Assignee: HORTUS NOVUS SRL, L'Aquila (AQ) (IT)

( * ) Notice: Subject to any disclaimer, the term of this patent is extended or adjusted under 35 U.S.C. 154(b) by 0 days.

(21) Appl. No.: 15/509,367

(22) PCT Filed: Sep. 18, 2015

(86) PCT No.: PCT/IB2015/057203
§ 371 (c)(1),
(2) Date: Mar. 7, 2017

(87) PCT Pub. No.: WO2016/042528
PCT Pub. Date: Mar. 24, 2016

(65) Prior Publication Data
US 2017/0273998 A1    Sep. 28, 2017

(30) Foreign Application Priority Data
Sep. 19, 2014 (IT) .............................. MI2014A1621

(51) Int. Cl.
| A61K 31/7028 | (2006.01) |
| A23L 33/105 | (2016.01) |
| A61K 9/00 | (2006.01) |
| A61K 36/88 | (2006.01) |
| A61K 9/20 | (2006.01) |
| A61K 31/12 | (2006.01) |
| A61K 31/352 | (2006.01) |
| A61K 31/05 | (2006.01) |
| A23L 33/00 | (2016.01) |

(52) U.S. Cl.
CPC ........ *A61K 31/7028* (2013.01); *A23L 33/105* (2016.08); *A23L 33/40* (2016.08); *A61K 9/0053* (2013.01); *A61K 9/20* (2013.01); *A61K 31/05* (2013.01); *A61K 31/12* (2013.01); *A61K 31/352* (2013.01); *A61K 36/88* (2013.01); *A23V 2002/00* (2013.01)

(58) Field of Classification Search
None
See application file for complete search history.

(56) References Cited

U.S. PATENT DOCUMENTS

| 2004/0076691 A1 | 4/2004 | Haines |
| 2014/0141082 A1 | 5/2014 | Gao |

FOREIGN PATENT DOCUMENTS

| CN | 103070877 A | 5/2013 |
| ES | 2428665 A1 | 11/2013 |
| GB | 2483121 A | 2/2012 |
| WO | 2014145316 A1 | 10/2015 |
| WO | 2015145316 A1 | 10/2015 |

OTHER PUBLICATIONS

U.S. Appl. No. 15/129,019, filed Sep. 2016, Bisti; Silvia.*
Esmael Tamaddonfard et al., "Effects of intraperitoneal and intracerebroventricular injection of crocin on acute corneal pain in rats," Phytotherapy Research, vol. 24, No. 10, May 17, 2010, pp. 1463-1467.
Alavizadeh Seyedeh Hoda et al., "Bioactivity assessment and toxicity of crocin: A comprehensive review," Food and Chemical Toxicology, vol. 64, Nov. 22, 2013, pp. 65-80.
Nagaki Yasunori et al., "Effects of oral administration of Gardeniae fructus extract and intravenous injection of crocetin on lipopolysaccharide- and prostaglandin E2-induced elevation of aqueous flare in pigmented rabbits," American Journal of Chinese Medicine, vol. 31, No. 5, 2003, pp. 729-738.
Fantes, Francisco E. et al, Wound healing after excimer laser keratomileusis (photorefractive keratectomy) in monkeys, 1990, (33 pgs.).
PCT International Search Report and Written Opinion dated Dec. 7, 2015 for Intl. App. No. PCT/IB2015/057203, from which the instant application is based, 13 pgs.
Carmona, Manuel et al., "Influence of Different Drying and Aging Conditions on Saffron Constituents," J. Agric. Food Chem. 2005, 53, 3974-3979.
Cossignani, Lina et al., Characterisation of secondary metabolites in saffron from central Italy, Food Chemistry 143 (2014), 446-451.
D'Archivio, Angelo Antonio et al., "Geographical classification of Italian saffron (*Crocus sativus* L.) based on chemical constituents determined by high-performance liquid-chromatography and by using linear discriminant analysis," Food Chemistry 212 (2016), 110-116.
Falsini, Benedetto et al., "Influence of Saffon Supplementation on Retinal Flicker Sensitivity in Early Age-Related Macular Degeneration," IOVS, Dec. 2010, vol. 51, No. 12, 6118-6124.
Maccarone, Rita et al, "Saffron Supplement Maintains Morphology and Function after Exposure to Damaging Light in Mammalian Retina," IOVS, Mar. 2008, vol. 49, No. 3, 1254-1261.
Mandal, Md Nawajes A. et al., "Curcumin protects retinal cells from light-and oxidant stress-induced cell death," Free Radical Biology & Medicine 46 (2009), 672-679.
Marangoni, Dario et al., "Functional effect of Saffron supplementation and risk genotypes in early age-related macular degeneration: a preliminary report," Journal of Translational Medicine 2013, 11:228, 11 pages.
Raskin, Ilya et al., "Can an Apple a Day keep the Doctor Away?" Current Pharmaceutical Design, 2004, 10, 3419-3429.
Tarantilis, Petros A. et al., "Determination of saffron (*Crocus sativus* L.) components in crude plant extract using high-performance liquid chromatography-UV-visible photodiode-array detection-mass spectrometry," Journal of Chromatography A, 699 (1995) 107-118.

(Continued)

*Primary Examiner* — Michael Barker
(74) *Attorney, Agent, or Firm* — Fredrikson & Byron, P.A.

(57) ABSTRACT

The present invention relates to a pharmaceutical, dietary and/or food composition, comprising saffron for use in the prevention and/or treatment of corneal dystrophies. The present invention also relates to a combination comprising saffron and at least one antioxidant and to a pharmaceutical dietary and/or food composition comprising said combination for use in the prevention and/or treatment of corneal dystrophies.

21 Claims, 2 Drawing Sheets

(56) References Cited

OTHER PUBLICATIONS

Xuan, Bo et al., "Effects of Crocin Analogs on Ocular Blood Flow and Retinal Function," Journal of Ocular Pharmacology and Therapeutics, vol. 15, No. 2, 1999, 143-152.
Vasireddy, Vidyullatha et al., "Rescue of Photoreceptor Degeneration by Curcumin in Transgenic Rats with P23H Rhodopsin Mutation," PLoS ONE, Jun. 2011, vol. 6, Issue 6, 10 pages.
Falsini, Benedetto et al., "Retinal Sensitivity to Flicker Modulation: Reduced by Early Age-Related Maculopathy," IOVS, May 2000, vol. 41, No. 6, 1498-1506.
Natoli, Riccardo et al., "Morphological, functional and gene expression analysis of the hyperoxic mouse retina," Experimental Eye Research, 92 (2011), 306-314.
PCT International Search Report and Written Opinion dated Jun. 8, 2015 for Intl. App. No. PCT/IB2015/052053, 11 pages.
International Preliminary Report on Patentability dated Apr. 18, 2016 for International Patent Application No. PCT/IB2015/052053, 7 pages.

\* cited by examiner

COMPOSITIONS BASED ON SAFFRON FOR THE PREVENTION AND/OR TREATMENT OF CORNEAL DYSTROPHIES

RELATED APPLICATIONS

This application is a 35 U.S.C. 371 national stage filing from International Application No. PCT/IB2015/057203, filed Sep. 18, 2015, which claims priority to Italian Application No. MI2014A001621, filed Sep. 19, 2014, the teachings of which are incorporated herein by reference.

The present invention is direct to a pharmaceutical, dietary and/or food composition, comprising saffron for use in the prevention and/or treatment of corneal dystrophies.

The present invention is also direct to a combination comprising saffron and at least one antioxidant and to a pharmaceutical dietetic and/or food composition comprising said combination for use in the prevention and/or treatment of corneal dystrophies.

PRIOR ART

The transparency of the cornea is essential to maintain visual function and depends on the perfect integrity of all the components thereof.

Corneal dystrophies are a group of progressive disorders of non-inflammatory nature, usually bilateral and mostly genetically determined, which cause opacification of the cornea.

They are characterised by a morpho-functional alteration resulting from modifications in normal corneal trophism and by abnormal accumulation of foreign matter in one or more of the five layers of the cornea, namely the epithelium, Bowman's layer, stroma, Descemet's membrane, and the endothelium. This material can cause the loss of transparency in the cornea or significant impairment of visual acuity.

One symptom common to many forms of corneal dystrophy is recurrent corneal erosion, where the outermost layer of the cornea (epithelium) does not adhere correctly to the eye. Recurrent conical erosion can cause discomfort or pain, abnormal sensitivity to light (photophobia), the feeling of a foreign body in the eye, and blurred vision.

Recurrent corneal erosion can be treated with specific contact lens (soft bandage) or with antibiotics such as doxycycline.

Doxycycline can, however, cause several side effects and can interfere with many drugs.

The age of corneal dystrophies onset varies from the first to fourth decade, depending on the relative frequency of recurrent epithelial erosions and vision deficit.

Corneal dystrophies can be classified into three groups based on the sole or predominant anatomical location of the anomalies: some affect primarily the corneal epithelium (epithelial corneal dystrophies), some the Bowman's layer (corneal dystrophies of Bowman's layer), others the corneal stroma (stromal corneal dystrophies), or the Descemet's membrane and the corneal endothelium (posterior or endothelial corneal dystrophies).

The group of epithelial corneal dystrophies includes epithelial basement membrane dystrophy (also known as "map-dot-fingerprint dystrophy" or anterior corneal dystrophy) and Meesmann's dystrophy.

Possible corneal dystrophies of the Bowman's layer include Reis-Bucklers dystrophy, Thiel-Behnke dystrophy, and Schnyder's central crystalline dystrophy. The group of stromal corneal dystrophies includes lattice corneal dystrophy, lattice corneal dystrophy type 1 (Biber-Haab-Dimmer), lattice corneal dystrophy type 2 (Meretoja syndrome), lattice corneal dystrophy types 3 and 3A, Avellino dystrophy, macular corneal dystrophy and gelatinous drop dystrophy. The endothelial corneal dystrophies include Fuchs' endothelial dystrophy and posterior polymorphous dystrophy.

Corneal dystrophy is the most common epithelial basement membrane dystrophy (EBMD).

It is a bilateral anterior corneal dystrophy, characterised by the presence, within the epithelium, of greyish lines in a fingerprint pattern, of irregular map-like areas with ground-glass appearance, and of small opaque spheroidal alterations (microcysts) visible under slit lamp examination.

The 50% of patients presenting recurrent corneal erosions are suffering from EBMD.

Treatment of corneal dystrophies usually involves the use of tear substitutes or, in cases of severe impairment of visual acuity, laser use is necessary or a corneal transplant must be performed.

Therefore, there is a need to find alternative therapies, preferably neither surgical nor invasive, which are effective in the prevention and/or treatment of corneal dystrophies without generating side effects.

Saffron, that is the stigmas of the *Crocus Sativus* plant, is known for its antioxidant/anti-inflammatory activity. Recently, it was shown that its crude extract, and purified derivatives thereof, are able to prevent tumors formation, atherosclerosis, and liver and kidney damage.

The chemistry of saffron is complex and there are many types of saffron, obtained from different varieties and differently prepared, which differ in the amount of their main components, such crocins, picrocrocin, campherols and safranal. Chemically, crocins are compounds of formula I, that is diesters of the dicarboxylic acid crocetin, wherein the carboxy groups are esterified by $R_1$ and $R_2$, wherein both $R_1$ and $R_2$ groups may be, independently, gentiobiose, glucose and many other sugars:

Formula I

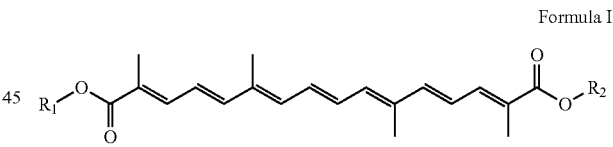

Different crocins may therefore be distinguished, in which the crocetin acid groups are esterified with different saccharides.

In the different varieties of saffron, the more abundant crocins are trans-crocin T1 (trans-crocin-4-gentiobiose-gentiobiose), of formula II Formula II

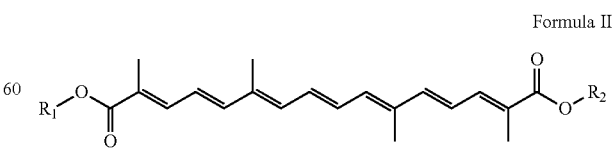

where $R_1=R_2=$gentiobiose, and trans-crocin T2 (trans-crocin-3-gentiobiose-glucose), of formula III Formula III

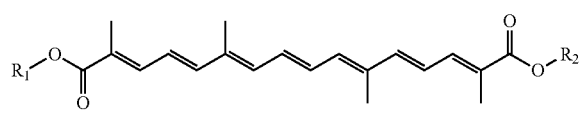

$R_1$=gentiobiose and $R_2$=glucose.

Also belong to the group of crocins analogues which have a different configuration of the 5-6 double bond of crocetin alkyl chain, i.e. compounds that have the cis configuration instead of the trans configuration, so called cis-crocins. The investigations carried out on varieties of saffron of different geographical origin have revealed that these different varieties of saffron mainly differ in their contents of trans and cis crocins.

The main object of the present invention is to provide a composition which allows treatment and also prevention of corneal dystrophies.

By "treatment", according to the present invention, it is meant the complete remission of the disease, but also the arrest or even a partial improvement of the recognized symptoms of corneal dystrophies existing at the beginning of therapy. By "prevention", according to the present invention, it is meant the administration of a medicament which slows down or inhibits the onset of the symptoms of corneal dystrophies; preferably, the administration as a preventive measure is indicated for genetically predisposed patients, or those presenting a gene mutation typical of the aforementioned corneal dystrophies, or for which have already been diagnosed with corneal dystrophy of genetic origin.

DESCRIPTION OF THE INVENTION

This object is achieved with a pharmaceutical, dietary and/or food composition, containing effective amounts of saffron.

An object of the present invention is therefore to provide a pharmaceutical, dietary and/or food composition, preferably a food supplement, containing effective amounts of saffron for use in the treatment and/or prevention of corneal dystrophies.

The corneal dystrophies to which the present invention is addressed are epithelial corneal dystrophies, Bowman's layer corneal dystrophies, stromal corneal dystrophies, or posterior or endothelial corneal dystrophies.

Preferably, the corneal dystrophies to which the present invention is addressed are the epithelial corneal dystrophies, and more preferably epithelial basement membrane dystrophy (EBMD).

By "saffron" in the present invention it is meant a mixture comprising crocins, picrocrocin, campherols and safranal, obtained through the pulverisation of the stigmas of *crocus sativus*.

In a preferred aspect, the saffron contained in the composition of the invention is a mixture in which the trans-crocin-4-gentiobiose-gentiobiose is present in an amount equal to or greater than 16.9% by weight, based on the total weight of saffron, and in which the trans-crocin-3-gentiobiose-glucose is preferably present in an amount equal to or higher than 8% by weight, based on the total weight of the saffron.

A further aspect of the present invention is a pharmaceutical, dietary and/or food composition comprising effective amounts of saffron in association with at least one physiologically acceptable excipient in the same dosage unit.

The daily dose and the duration of the treatment vary according to the treatment indication, the age and the patient's clinical situation.

The use of said composition for the prevention and/or treatment of corneal dystrophies provides for the daily dose administration of saffron ranging between 5 and 50 mg/day, preferably ranging between 10 and 40 mg/day, still more preferably a daily dose of 20 mg/day or 30 mg/day.

Preferably, said composition is administered with a posology of one daily dose, as stated above, divided into two doses over the day (morning and evening).

It was also shown that the combination of saffron with a proper amount of at least one antioxidant allows obtaining a further advantage in terms of effectiveness in the prevention and/or treatment of corneal dystrophies.

A further object of the present invention is therefore a pharmaceutical, dietary and/or food composition, preferably a food supplement, containing effective amounts of saffron in combination with effective quantities of at least one antioxidant for use in the treatment and/or prevention of corneal dystrophies. Preferably, the antioxidant belongs to the polyphenols class; still more preferably, said antioxidant is selected from the group comprising flavonoids, such as quercetin and curcumin, and stilbenes, such as resveratrol.

Still more preferably, the antioxidant is selected from the group comprising quercetin, curcumin, and resveratrol.

The composition of the invention comprising the combination of saffron and at least one antioxidant can perform greater activity than a composition containing the saffron or the antioxidant alone, thereby demonstrating a synergistic effect due to the combination of saffron and the antioxidant.

In a further aspect, the present invention is directed to pharmaceutical, dietary and/or food composition, comprising saffron, in which the amount of trans-crocin-4-gentiobiose-gentiobiose is present in an amount equal to or greater than 16.9% by weight, based on the total weight of the saffron, and in which trans-crocin-3-gentiobiose-glucose is preferably present in an amount equal to or greater than 8% by weight, based on the total weight of the saffron, and at least one antioxidant and in combination with at least one physiologically acceptable excipient, for use in the prevention and/or treatment of corneal dystrophies.

The use of said composition and/or combination for the prevention and/or treatment of corneal dystrophies provides for the daily dose administration of saffron ranging between 5 and 50 mg/day, preferably ranging between 10 and 40 mg/day, still more preferably a daily dose of 20 mg/day or 30 mg/day, in combination with an amount of at least one antioxidant ranging between 50 and 250 mg/day, preferably 100 mg/day or 200 mg/day.

In a particularly preferred aspect of the present invention, the combination of saffron and at least one antioxidant is characterised in that said saffron is administered at a daily dose of 20 mg/day or 30 mg/day and said at least one antioxidant, selected from the group comprising quercetin, curcumin and resveratrol, is administered at a daily dose of 100 mg/day or 200 mg/day.

Preferably, said combination of saffron and at least one antioxidant is administered with a posology of one daily dose, as stated above, divided into two doses over the day (morning and evening).

In a preferred aspect, the pharmaceutical, dietary and/or food compositions in this invention are administered systemically, in particular orally.

The pharmaceutical, dietary and/or food compositions of the present invention are preferably formulated in a solid form, said solid form being selected from tablet, granulate, dragee, or capsule, and more preferably tablet.

To obtain the pharmaceutical dietary and/or food compositions, according to the present invention the following classes of known excipients are preferably used: anti-caking agents, sweeteners, surfactants (cationic, anionic or non-ionic), diluents, aggregating agents or binders, lubricants, glidants, stabilisers, solubilizers, emulsifiers, humectants, flavourings, coating agents, colouring agents, acidity regulators, or a mixture thereof.

In one preferred aspect, the pharmaceutical, dietary and/or food compositions of this invention comprise saffron and at least one antioxidant, wherein said antioxidant preferably belongs to the polyphenol class, still more preferably, said antioxidant is selected from the group comprising flavonoids, such as quercetin and curcumin, and stilbenes, such as resveratrol, in association with at least one physiologically acceptable excipient in the same dosage unit in tablet form for oral administration.

In a preferred aspect, the combination and/or the pharmaceutical compositions of this invention are administered to mammals, especially to humans.

BRIEF DESCRIPTION OF THE FIGURES

Additional features and advantages of the invention will become more clearly apparent by the following description of some preferred embodiments thereof, given hereinbelow by way of illustration and not of limitation, with reference to the attached drawings. In such drawings.

Figure 1:
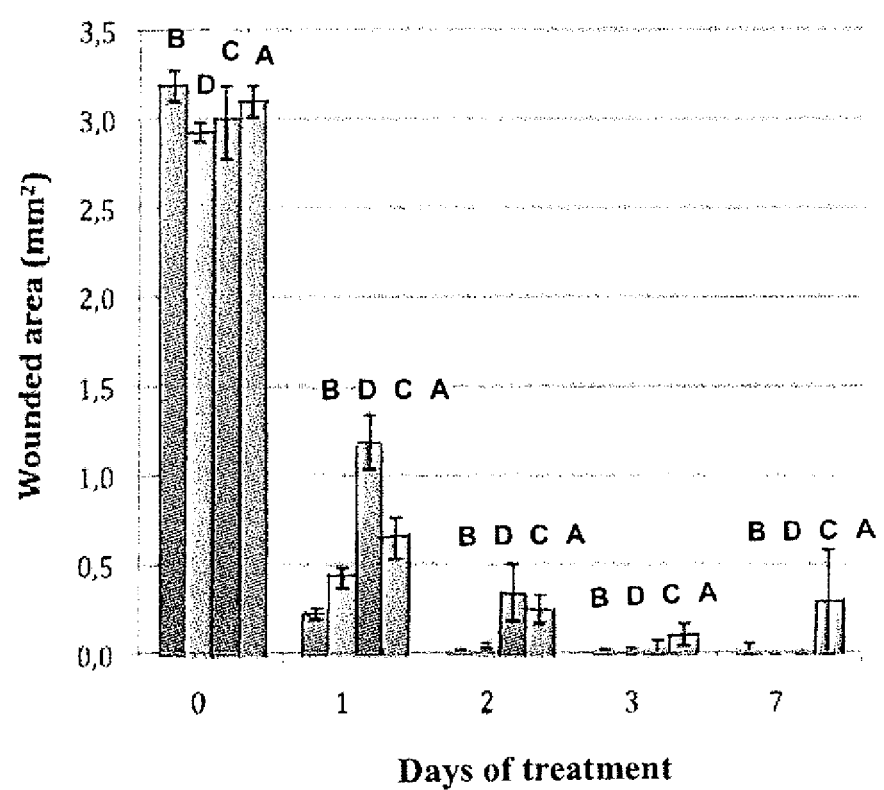
FIG. 1 is a graph illustrating the size of the damaged area (mm$^2$), in the four experimental groups (A-D), over the course of the seven days following surgery.

The following examples are intended to better understand the invention, without in any way limiting it.

EXPERIMENTAL PART

Example 1

It has been demonstrated that administration of a composition comprising effective doses of saffron to a patient suffering from epithelial basement membrane dystrophy was effective in the treatment of such disease.

The epithelial basement membrane dystrophy had been diagnosed based on clinical manifestations of recurrent corneal erosions and infections that the patient had suffered for several years prior to start drug-based treatment.

The patient complained of acute pain in the eyes, above all during the latter stages of sleep and upon waking.

The patient had initially been treated with steroids and doxycycline (100 mg/day) for 10 months, with concomitant use of tear substitutes.

The treatment proved effective and the symptoms subsided.

Nevertheless, the discontinuation of the doxycycline resulted in the return of the symptoms within a few days and likewise the acknowledged side effects.

The patient discontinued treatment with doxycycline and subsequently started treatment with two tablets per day of a saffron composition containing:

| | |
|---|---|
| saffron | 10 mg |
| curcumin | 50 mg |

The patient immediately noted the absence of symptoms related to recurrent corneal erosions.

Given the tolerability of the composition, treatment with saffron was continued and today, approximately two years after starting treatment, the patient is no longer suffering from any symptoms.

Example 2

A patient suffering from epithelial basement membrane dystrophy and the same clinical history as described in Example 1 was treated with two tablets per day of a saffron composition containing:

| | |
|---|---|
| saffron | 15 mg |
| quercetin | 50 mg |
| resveratrol | 50 mg |

The patient immediately noted the absence of symptoms related to recurrent corneal erosions.

The treatment with saffron was continued and today, approximately two months after starting treatment, the patient is no longer suffering from any symptoms.

It has therefore been demonstrated that administration of a composition comprising effective doses of saffron, quercetin and resveratrol to a patient suffering from epithelial basement membrane dystrophy was effective in the treatment of such disease.

Example 3

A patient suffering from epithelial basement membrane dystrophy and the same clinical history as described in Example 1 was treated with two tablets per day of a saffron composition containing:

| | |
|---|---|
| saffron | 10 mg |

The patient immediately noted the absence of symptoms related to recurrent corneal erosions.

During treatment with saffron, the patient stopped taking steroids and doxycycline and only used the tear substitutes occasionally.

Today, approximately two years after starting treatment, the patient is no longer suffering from any symptoms.

Example 4

(Evaluation of the Effects of Orally Administered Saffron Solution on the Corneal Wound Healing Process on a Murine Model of Surgical Corneal Lesion)

For the experiment, 40 animals (mice) of the MUS MUSCULUS species were used, all male, healthy, and aged three months.

The saffron used had an amount of trans-crocin-4-gentobiosio-gentobiosio amounting to 16.9% and of trans-crocin-3-gentobiosio-glucose amounting to 8%. Both eyes of each mouse were subjected to PRK (photorefractive keratectomy), which consists of a surgery on the central cornea, with a 2 mm ablation area, 45 microns of depth (reaching the epithelium), using an excimer laser.

The corneal wound healing process was monitored using a stereoscopic microscope, immediately after surgery and at 1, 2, 3 and 7 days thereafter. With a colorimetric test with fluorescein (Alcon Cusí, Barcelona, Spain) the degree of damage to the corneal epithelium was evaluated. This is because the fluorescein accumulates in the areas where the epithelium is damaged; with the wound healing evolution, the marked (coloured) area decreases. The level of opacity of the cornea was evaluated according to the method of Fante et al. (1990) which involves four levels of opacity, ranging from 0 to 4, where 0=completely clear cornea, 4=severe opacity. All clinical evaluations were performed separately, by two operators.

The animals were divided into four experimental groups:

Group A: mice with corneal injury, not treated with saffron (drinking water only);

Group B: mice with corneal injury, treated with aqueous saffron solution;

C and D are used to show the groups of animals used as an internal control, which were treated, respectively, with plasma rich in PRGF and Cacicol growth factors (CACICOL-RGTA 20; Thea Laboratoires). The saffron treatment was orally administered (in the diet), while in the two control groups, the treatment was administered topically.

The ocular features were studied daily just before administration of treatments by microscopic analysis. Each group was analysed at four times: 1, 2, 3 and 7 days of treatment. These time points were selected because they include important events in the wound healing process.

In the following Table I the experimental schedule is summarised:

TABLE I

| Group | Treatment | | Doses | Sacrifice time | N. of animals |
| | Left eye injured | Right eye injured | | | |
|---|---|---|---|---|---|
| A | water | water | ad libitum | 7 days | 10 |
| B | Saffron solution | Saffron solution | 5 mg/kg | 7 days | 10 |
| C | PRGF | PRGF | 2.5 µL/eye | 7 days | 10 |
| D | Cacicol | Cacicol | 2.5 µL/eye | 7 days | 10 |

* "Sacrifice time" it is meant the number of days from the surgery through to the time at which the animal is sacrificed.

The aqueous saffron solution was administered daily by syringe at a dose of 5 mg/kg/day. The volume of solution administered was 300 µl/day. All the treatments (saffron, PRGF, and Cacicol) began seven days prior to surgery and were ended seven days later, with the death of the animal.

The ocular features were evaluated daily by microscopic analysis. After the sacrifice, the eyes were enucleated and duly processed for immune histological analysis.

Figure 2:
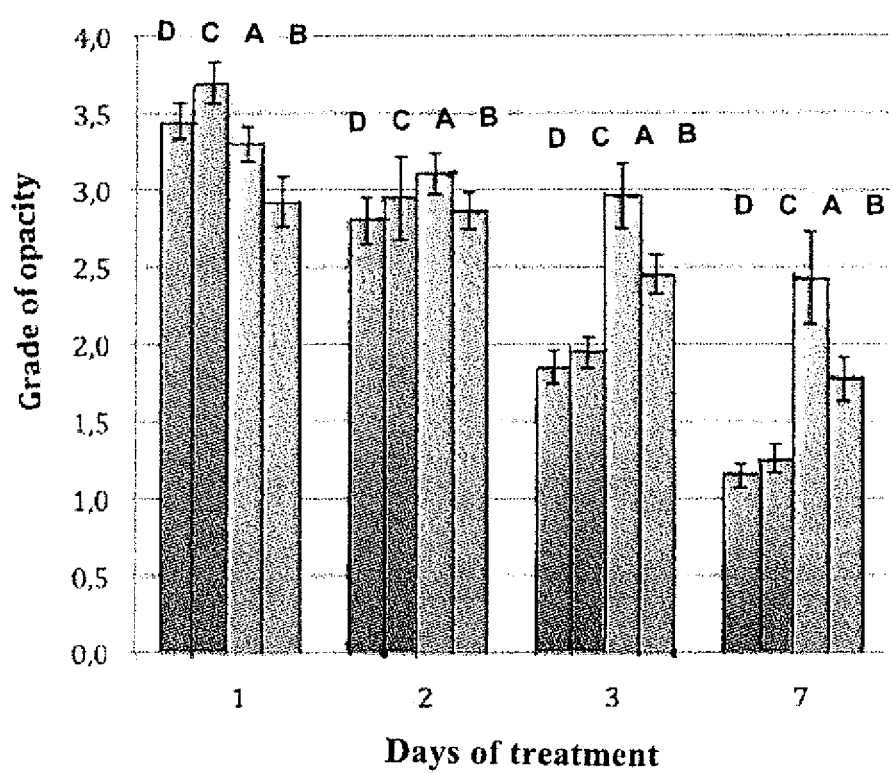
FIG. 2 is a graph illustrating the degree of opacity in the four experimental groups (A-D), over the course of the seven days following surgery.

The results are shown in FIGS. 1 and 2, wherein the data is expressed, respectively, in units of damaged surface area (mm$^2$) and degree of opacity during the seven days following surgery.

With reference to FIG. 1, 1 day after surgery, the greater re-epithelialisation efficiency corresponds to treatment with the saffron solution according to the invention—group B (0.22±0.02 mm). This value is lower than that obtained with the Cacicol—group D (0.43±0.06 mm), although the difference between the two groups was not statistically significant. Significant differences were observed between the untreated control group (A; 0.65±0.11 mm) and the saffron group (B), whereas treatment with Cacicol (group D) showed no significant differences from the mice drinking only water (group A). Treatment with PRGF (group C) was found to be the least efficient in terms of reduction of the injured area (1.19±0.15 mm) with marked differences with respect to the other groups. On the second day, there were no statistically significant differences between the groups, although the smallest average injured area observed was that of the saffron group, in accordance with the invention, i.e. group B (0.02±0.01 mm). Also on the third day, no significant differences between the groups were observed. 7 days after surgery, most of the eyes had completely repaired at the level of the epithelium, while the group treated with drinking water (A) presented epithelial ulcers in 12.5% of cases and the PRGF group (C) in 10% of cases. A 100% success rate was observed in the animals treated with Cacicol (group D) and with saffron (group B).

With reference to FIG. 2, following surgery on the cornea, the tissue became very opaque during the first 24 hours, due to inflammatory processes and oedema. All the groups observed one day after surgery showed a degree of corneal opacity greater than or equal to 3 according to the Fantes' scale.

Two days after treatment, the degree of opacity decreased slightly with respect to level 3 in all groups, except the untreated group (group A), even though statistically significant differences between groups can be observed. On the third day of analysis, there was a marked difference between the groups. Treatment with Cacicol (group D), PRGF (group C), and saffron (group B) significantly improved corneal transparency quality. The Cacicol and PRGF treatments showed opacity levels below level 2, while the saffron group showed an average opacity value of (2.15±0.12). Statistically significant differences between the saffron and Cacicol/PRGF groups were observed on the third day. The seventh day after surgery was particularly interesting because that was when the positive controls (Cacicol and PRGF) showed an optimal degree of corneal transparency. After seven days, the saffron group, according to the invention (group B), showed a significant reduction in corneal opacity, which settled at an average value of (1.77±0.14).

In terms of speed of epithelial healing, treatment with the aqueous solution of saffron for a duration of 14 days (7 prior to surgery and 7 days after) was as efficient as the Cacicol (which is considered the best treatment in the healing process) and was significantly better than treatment with PRGF. The saffron also significantly reduced the level of opacity compared with the untreated mice (drinking water only), although it was less effective than the other substances such Cacicol or PRGF. Regarding this, it is important to note that the administration route differed for each substance: the Cacicol and the PRGF were applied directly to the cornea, while the saffron solution was administered systemically. The concentration of an active ingredient administered by oral route which acts in the cornea healing process cannot be determined with respect to a topical treatment (drops), but this shows that, although administered systemically, saffron can reduce the level of opacity.

Therefore it has been demonstrated that the orally treatment with saffron, according to the invention, serves in the re-epithelisation of the cornea.

The invention claimed is:

1. A method of treating and/or preventing corneal dystrophies in a mammal comprising administering a pharmaceutical, dietary and/or food composition to the mammal, wherein the pharmaceutical, dietary and/or food composition contains effective amounts of saffron.

2. The method according to claim 1, characterised in that said saffron comprises trans-crocin-4-gentiobiose-gentiobiose present in an amount equal to or higher than 16.9% by weight with respect to a total weight of the saffron.

3. The method according to claim 1, characterised in that said saffron comprises trans-crocin-3-gentiobiose-glucose.

4. The method according to claim 1, characterised in that the corneal dystrophies are selected from the group consisting of epithelial corneal dystrophies, corneal dystrophies of Bowman's layer, stromal corneal dystrophies, posterior corneal dystrophies, and endothelial corneal dystrophies.

5. The method according to claim 4, characterised in that said corneal dystrophies are epithelial corneal dystrophies.

6. The method according to claim 5, characterised in that said corneal dystrophies comprise epithelial basement membrane dystrophy.

7. The method according to claim 1, characterised in that said saffron is administered at a daily dose comprised between 5 and 50 mg/day.

8. The method according to claim 1, characterised in that the pharmaceutical, dietary and/or food composition further comprises effective amounts of at least one antioxidant.

9. The method according to claim 8, characterised in that said at least one antioxidant is a polyphenol.

10. The method according to claim 9, characterised in that said polyphenol is selected from the group consisting of quercetin, curcumin and resveratrol.

11. The method according to claim 8, characterised in that said saffron is administered at a daily dose comprised between 5 and 50 mg/day, and said antioxidant is administered at a daily dose of between 50 and 250 mg/day.

12. The method according to claim 1, wherein the mammal is a human.

13. The method according to claim 1, wherein the pharmaceutical, dietary and/or food composition further comprises at least one physiologically acceptable excipient.

14. The method according to claim 1, wherein the pharmaceutical, dietary and/or food composition is a tablet, granulate, dragee or capsule.

15. The method according to claim 1, wherein the pharmaceutical, dietary and/or food composition is a food supplement.

16. The method according to claim 7, wherein the daily dose of saffron administered to the mammal is between 10 mg/day and 40 mg/day.

17. The method according to claim 16, wherein the daily dose of saffron administered to the mammal is 20 mg/day or 30 mg/day.

18. The method according to claim 11, wherein the daily dose of saffron administered to the mammal is between 10 mg/day and 40 mg/day.

19. The method according to claim 18, wherein the daily dose of saffron administered to the mammal is 20 mg/day or 30 mg/day, and the daily dose of antioxidant administered to the mammal is 100 mg/day or 200 mg/day.

20. The method according to claim 14, wherein the pharmaceutical, dietary and/or food composition is a tablet.

21. The method according to claim 3, wherein the trans-crocin-3-gentiobiose-glucose is present in an amount equal to or higher than 8% by weight with respect to a total weight of the saffron.

* * * * *